United States Patent [19]

Prasad

[11] 4,419,325
[45] Dec. 6, 1983

[54] DENTAL ALLOYS FOR PORCELAIN-FUSED-TO-METAL RESTORATIONS

[75] Inventor: Arun Prasad, Cheshire, Conn.

[73] Assignee: Jeneric Industries, Inc., Wallingford, Conn.

[21] Appl. No.: 400,481

[22] Filed: Jul. 21, 1982

[51] Int. Cl.³ .................... C22C 5/04; C22C 30/02
[52] U.S. Cl. .................... 420/464; 420/508; 420/580; 420/587
[58] Field of Search .............. 420/463, 464, 508, 580, 420/587; 433/207, 222, 200

[56] References Cited

U.S. PATENT DOCUMENTS

| | | | |
|---|---|---|---|
| 2,050,077 | 11/1936 | Wise | 420/587 |
| 2,105,312 | 3/1938 | Cohn | 420/463 |
| 2,132,116 | 10/1938 | Kiepe | 420/464 |
| 2,143,217 | 1/1939 | Truthe | 420/590 |
| 2,172,512 | 9/1939 | Kilgallon | 420/464 |
| 3,134,671 | 5/1964 | Prosen | 420/465 |
| 3,155,467 | 11/1964 | Yamamoto et al. | 420/463 X |
| 3,438,770 | 6/1969 | Clark et al. | 420/456 |
| 3,666,540 | 5/1972 | Burnett | 420/509 X |
| 3,819,366 | 6/1974 | Katz | 420/463 |
| 3,928,913 | 12/1975 | Schaffer | 420/463 X |
| 3,989,515 | 10/1976 | Reiff | 420/464 |
| 4,063,937 | 11/1977 | Goltsov et al. | 420/463 |
| 4,123,262 | 10/1978 | Cascone | 420/508 |
| 4,124,382 | 11/1978 | Prosen | 420/463 |
| 4,179,286 | 12/1979 | Knosp | 420/463 |
| 4,179,288 | 12/1979 | Prosen | 420/463 |
| 4,205,982 | 6/1980 | German | 420/508 |
| 4,261,744 | 4/1981 | Boyajian | 420/463 |
| 4,266,973 | 5/1981 | Guzowski et al. | 420/587 |
| 4,319,877 | 1/1982 | Boyajian | 420/463 X |
| 4,387,072 | 10/1983 | Schaffer | 420/463 |

FOREIGN PATENT DOCUMENTS

| | | | |
|---|---|---|---|
| 510640 | 8/1939 | United Kingdom | 420/464 |
| 1365271 | 8/1974 | United Kingdom | 420/465 |

Primary Examiner—Brian E. Hearn
Assistant Examiner—David A. Hey
Attorney, Agent, or Firm—Kramer and Brufsky

[57] ABSTRACT

A dental alloy for use in porcelain-fused-to-metal restorations including palladium, cobalt, gallium, gold, aluminum, copper and ruthenium or rhenium. The cobalt controls the coefficient of thermal expansion of the alloy to permit the use of the alloy with commercially available porcelains having a variety of thermal coefficients. The ruthenium of rhenium provides grain refining for the alloy to increase its elongation, tensile strength, and thus toughness. The alloy with ruthenium or rhenium as a grain refining agent must be made under vacuum or in an inert atmosphere to avoid the formation of bubbles in the porcelain during the porcelain firing process.

12 Claims, 9 Drawing Figures

DENTAL ALLOYS FOR PORCELAIN-FUSED-TO-METAL RESTORATIONS

BACKGROUND OF THE INVENTION

This invention relates to palladium based dental alloys and, in particular, to alloys for use in porcelain-fused-to-metal restorations.

Porcelain-fused-to-metal restorations consist of a metallic sub-structure coated with a veneer of porcelain. Over the years various alloys have been proposed for the sub-structure of these restorations. Many of the early alloys used gold with some platinum or palladium as the main alloy ingredients. However, with the increases and fluctuations in the price of gold and platinum in recent years, other alloys have come to play major roles in this area. One series of alloys which has gained general acceptance is based on nickel, chromium and beryllium as the main ingredients. Another series of alloys, with which this invention is concerned, is based on palladium as the dominant element.

One such palladium based alloy for use in porcelain-fused-to-metal restorations is described in U.S. Pat. No. 4,261,744. This alloy includes approximately 80% palladium and lesser amounts of indium, tin, cobalt and silicon. Another palladium alloy, which was commercially available prior to this invention, includes, based on spectrographic analysis, approximately 2% gold, 79% palladium, 9% gallium, 10% copper and perhaps a trace of boron (on the order of 0.1%). Alloys similar to this commercial alloy, which include gold, palladium gallium, copper and boron are described in U.S. Pat. Nos. 3,134,671 and 4,179,288.

In examining the commercially available gold-palladium alloy described above, it was found that the alloy suffered a number of disadvantages in terms of its suitability for use in porcelain-fused-to-metal restorations. In particular, the alloy exhibited poor grain structure which give it low elongation, lower than optimum tensile strength and low toughness, as well as making it susceptible to "hot-tearing" during the investment casting process.

Suprisingly, in seeking to overcome these limitations, numerous difficulties were encountered in attempting to grain refine this alloy. In particular, it was found that when the standard grain refining techniques were applied to the alloy, and the alloy then used to make a casting for a porcelain-fused-to-metal restoration, the casting caused bubbles to form in the porcelain during the porcelain firing process. This resulted in an unusable restoration.

Moreover it was found that the commercial gold-palladium alloy had a coefficient of thermal expansion which was not compatible with the full range of porcelains available for porcelain-fused-to-metal restorations. In particular, although the alloy could be used with porcelains having a low coefficient of thermal expansion, it could not be used with porcelains having a high coefficient, particularly for long-span bridgework involving pontics.

Accordingly, it is one of the objects of this invention to overcome the limitations of the above described commercially available palladium based dental alloy. In particular, it is an object of this invention to provide a grain refined palladium based dental alloy which will not produce bubbles when porcelain is applied. It is a further object of the invention to produce a palladium based dental alloy which has a coefficient of expansion compatible with the complete range of dental porcelains commonly used in porcelain-fused-to-metal restorations.

The attainment of these and other objects of the invention is described below in connection with the description of the preferred embodiments of the invention.

SUMMARY OF THE INVENTION

In accordance with the invention, a palladium based dental alloy is provided which consists essentially of approximately 35–85% by weight palladium, 0–12% by weight copper, 5–15% by weight gallium, 0–50% by weight gold, 0–5% by weight aluminum, 0–13% cobalt and 0.1–0.5% ruthenium or rhenium, the total of the constituents being 100%. Preferred embodiments of the alloy have approximate compositions by weight as follows:

| Pd   | Cu  | Ga | Au  | Al  | Co  | Ru or Re |
|------|-----|----|-----|-----|-----|----------|
| 78.7 | 10  | 9  | 2.0 | 0.1 | —   | 0.2      |
| 78.7 | 7.5 | 9  | 2.0 | 0.1 | 2.5 | 0.2      |
| 80.7 | —   | 9  | —   | 0.1 | 10  | 0.2      |

The ruthenium or rhenium in these alloys serves as a grain refining agent. In accordance with the invention, to introduce these agents, the alloy must be made either in a vacuum or under an inert atmosphere, such as an atmosphere of argon. If not done in this way, the alloy that is produced will cause bubbling of the porcelain during the porcelain firing process. Importantly, iridium, which is a known grain refining agent, is excluded from the invention because it fails to grain refine the alloy.

The cobalt serves to control the coefficient of thermal expansion of the alloy. The amount of this component is adjusted to provide coefficients of thermal expansion compatible with the complete range of porcelains available for porcelain-fused-to-metal restorations.

BRIEF DESCRIPTION OF THE DRAWINGS

In FIG. 1, the coefficient of expansion of the alloy is greater than that of the porcelain so that the porcelain is under longitudinal compression in the final fused product, as is desired. In contrast, FIG. 2 illustrates the undesirable situation where the porcelain is under longitudinal tension in the final fused product because the coefficient of thermal expansion of the alloy is less than the coefficient of thermal expansion of the porcelain. The changes in length shown in these figures are for purposes of illustration only, and are not to scale.

DESCRIPTION OF THE PREFERRED EMBODIMENTS

The alloys of this invention include seven constituents: gold, palladium, gallium, copper, aluminum, cobalt and ruthenium or rhenium.

Palladium and gold give the alloy its basic inertness so that it can withstand the environment of the patient's mouth. The relative amounts of these two components can be varied without changing the properties of the alloy.

Gallium and cobalt/copper reduce the melting point and strengthen the alloys. These components also form a protective and adherent oxide on the surface of the casting which reacts with the porcelain to produce a chemical bond. Of these elements, it was found that the combination of gallium and cobalt produces an oxide which is better for bonding porcelain than the oxide formed from the combination of gallium and copper.

The aluminum serves to protect the alloy during torch melting and also during the porcelain firing process. Specifically, as the alloy is torch melted prior to being cast, the aluminum forms an oxide on the outside of the metal. This oxide prevents the absorption of gases by the molten alloy. Such gases, if permitted to be absorbed, could later be released during the porcelain application process and thus form bubbles in the porcelain. Similarly, during the porcelain firing process, the aluminum forms a protective oxide when the metal substructure is heated.

The preferred concentration of aluminum is approximately 0.1% by weight. Higher amounts of aluminum can be used in place of gallium to lower the melting point and to strengthen the alloy.

Cobalt is used in the alloy to provide flexibility in the adjustment of the alloy's coefficient of thermal expansion. Gallium, copper and aluminum also affect the coefficient of thermal expansion, but to a much lesser extent. Flexibility in the ability to adjust the coefficient of thermal expansion is necessary in view of the broad range of porcelains available in the market.

Figure 1:
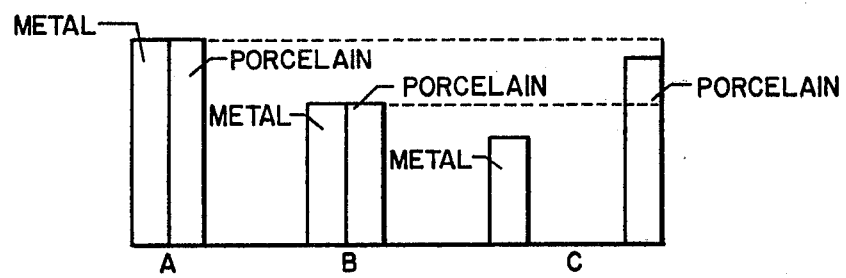
FIGS. 1 and 2 illustrate diagrammatically the importance of the relative coefficients of thermal expansion of the alloy and the porcelain.
Figure 2:
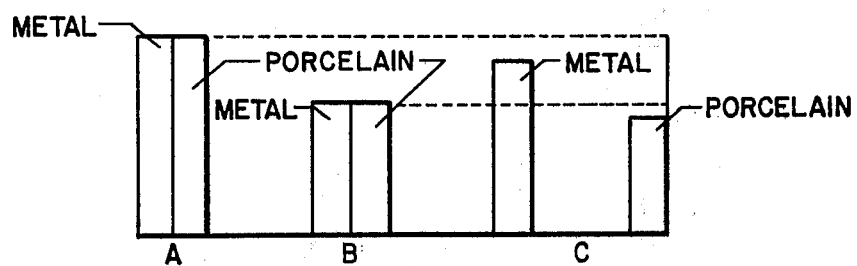

FIGS. 1 and 2 illustrate diagrammatically the effect on longitudinal contraction of different relative coefficients of thermal expansion for the porcelain and the alloy.

In FIG. 1, the metal is assumed to have a coefficient of expansion, and thus a coefficient of contraction, greater than that of the porcelain. Panel A of FIG. 1 shows the porcelain and alloy in their heated condition, just after the bond has formed between the porcelain and the oxides on the alloy. Panel B shows the porcelain and alloy, bonded together, in their cooled, contracted state. Panel C shows the contraction that would have occurred in the alloy and the porcelain is the two materials had not been bonded together.

Comparing panels B and C, we see that the metal component in panel C has a length shorter than the bonded porcelain-metal combination, while the porcelain component in panel C has a length greater than the bonded combination. Accordingly, for the bonded combination, the porcelain is under compression, because its length is less than the length it would have had if it had not been bonded to the alloy, while the alloy is under tension, because its length is greater than the length it would have had if it was not bonded to the porcelain.

FIG. 2 shows the identical set of conditions but for the coefficient of expansion of the metal being less than that of the porcelain. Again panel A shows the length of the alloy-porcelain combination in its heated condition. Panel B shows the length after cooling, and panel C shows the lengths the individual components would have had if they had not been bonded together. In this case, because the metal contracts less than the porcelain, the metal is under compression and the porcelain is under tension.

In terms of porcelain-fused-to-metal restorations, it is important that the porcelain be under compression, not tension. If it is under tension, cracks will form in the porcelain to relieve the tension. It is to achieve this condition of porcelain being under compression that varying amounts of cobalt are used in the alloy of this invention.

The following table illustrates the effect of varying the concentration of cobalt upon the thermal expansion of the alloy ($K_T$) at 500° C. The percentages shown in the first column of this table were determined using a Theta differential dilatometer, where the reference temperature was 30° C., the rate of temperature climb was 3° C./minute and the reference standard was pure platinum.

TABLE I

| Alloy | $K_T$ | Co | Cu | Pd | Ga | Al | Au | Ru |
|---|---|---|---|---|---|---|---|---|
| 1 | .640% | — | 10 | 78.7 | 9 | 0.1 | 2.0 | 0.2 |
| 2 | .655% | 2.5 | 7.5 | 78.7 | 9 | 0.1 | 2.0 | 0.2 |
| 3 | .695% | 10 | — | 78.7 | 9 | 0.1 | 2.0 | 0.2 |

Figure 3:
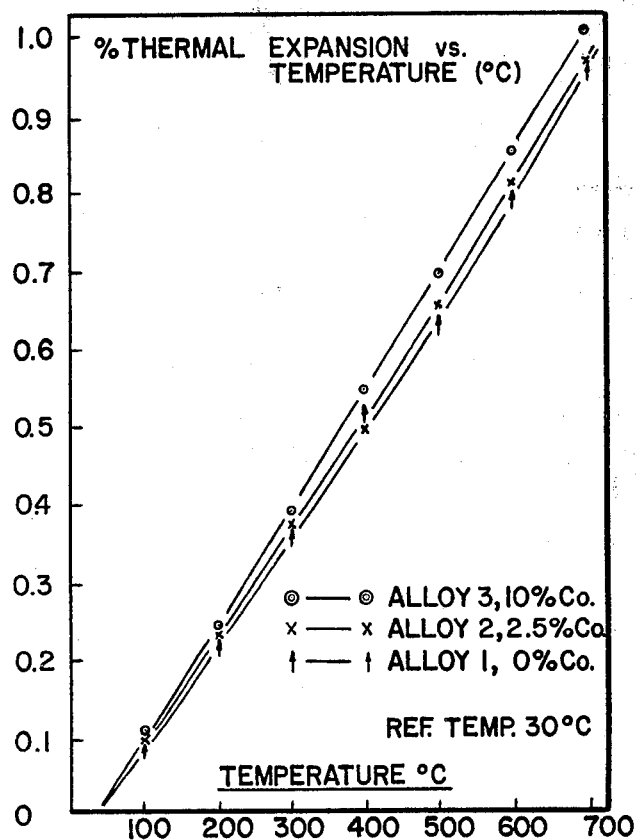
FIG. 3 is a plot of thermal expansion ($K_T$) versus temperature for three alloys having 10% cobalt (the upper curve), 2.5% cobalt (the middle curve) and no cobalt (the lower curve). The remainder of the composition of these alloys is given below in Table I.

FIG. 3 shows the behavior of $K_T$ over the range of temperatures from 30° C. to 700° C.

As can be seen from FIG. 3 and Table I, the substitution of cobalt for copper increases the amount of thermal expansion exhibited by the alloy with changes in temperature. This allows the production of alloys useful for a wide range of porcelains, in that, by adjusting the cobalt concentration, a thermal expansion for the alloy can be obtained which is greater than the thermal expansion of the porcelain so that, in the final restorations, the porcelain will be under compression.

The ruthenium or rhenium component of the alloy provides the important property of grain refining. Alloys consist of individual grains in contact with each other. The size of these grains is critical to the physical properties of the alloy. This size can vary from coarse to fine, and the grains can be regular or irregular.

Ideally, a dental alloy should have fine, regular grains. Alloys with this type of grain structure exhibit superior elongation, tensile strength and toughness properties. Moreover, such alloys are less prone to hot tearing during the investment casting process, as compared to alloys with a coarser grain structure. "Hot tearing", as understood in the art, involves the formation of cracks in the casting due to stresses produced in the casting as it cools in the investment. These cracks can result in failures which necessitate remaking the casting with the concomitant loss of the time, energy and material used to make the original casting.

In an attempt to improve the grain structure of the alloys of this invention ruthenium, rhenium and iridium were tested. Quite surprisingly, it was found that when these grain refiners were used, and the alloy was prepared in air, the conventional manufacturing technique for precious alloys, the resulting alloy was unsuitable for use in a porcelain-fused-to-metal restoration because it produced bubbles in the porcelain during the porcelain firing process. Only when the alloy was prepared in a vacuum or in an inert atmosphere, was a suitable alloy obtained. Moreover, when the grain refining element iridium was used, only poor grain refinement was achieved regardless of the particular method of preparation employed. This was found to be the case up to and including iridium concentrations as high as 0.5%.

Figure 4:
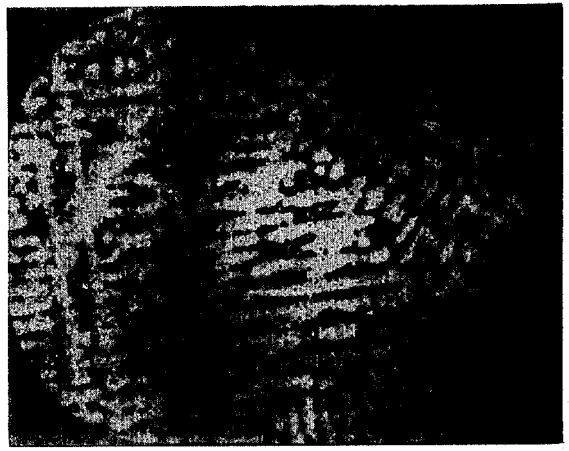
FIG. 4 is a photomicrograph showing the grain structure of the commercially available gold-palladium alloy discussed above.

FIGS. 4, 5, 6 and 7 show the effects of grain refining on the alloys of this invention. FIG. 4 is a photomicrograph of the grain structure of the commercially available gold-palladium alloy described above. As can be seen, the grain structure is coarse.

Figure 5:
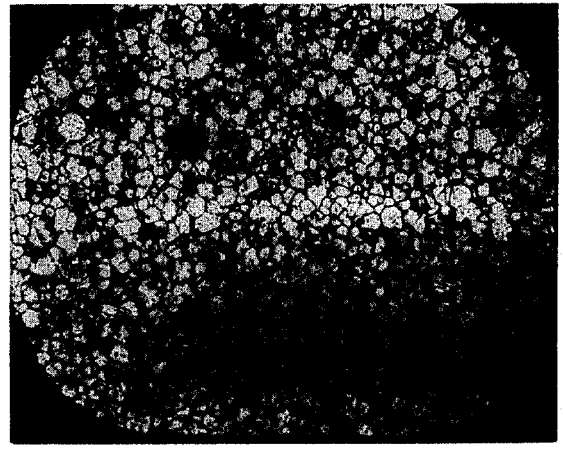
FIGS. 5 and 6 are photomicrographs showing the improved grain structure of the alloys of this invention when ruthenium (FIG. 5) or rhenium (FIG. 6) are used as grain refining agents.
Figure 6:
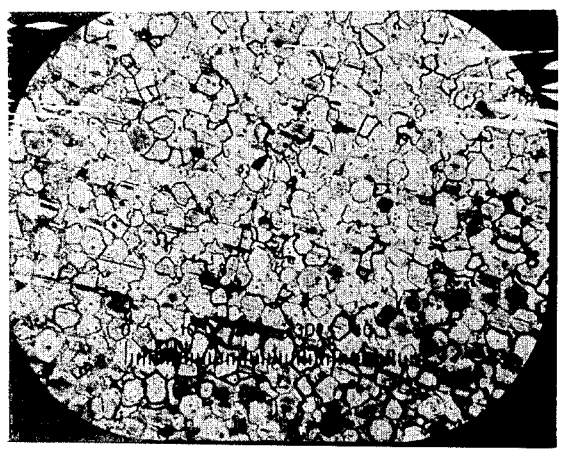

FIGS. 5 and 6 show the alloys of this invention where 0.2% by weight ruthenium or rhenium, respectively, have been added. The FIG. 5 alloy has the composition of alloy 1 in Table I; the FIG. 6 alloy has the same composition but with rhenium in place of ruthenium. As can be seen from these photomicrographs, the grain structure is now significantly improved in comparison to the commercially available alloy, and the alloy consists of regular, small grains.

Figure 7:
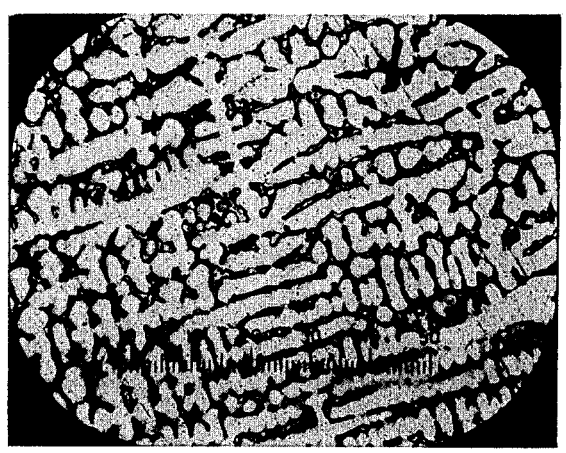
FIG. 7 is a photomicrograph showing the poor grain structure of the alloy when iridium is used as the grain refining agent.

FIG. 7 shows the situation when 0.2% iridium is used as a grain refiner. This alloy has the same composition as the alloys of FIGS. 5 and 6 but with iridium substituted for ruthenium or rhenium. Plainly, only very poor grain refining has been achieved and the grain of this alloy is more similar to that of the commercially available alloy (FIG. 4) than that achieved with ruthenium or rhenium (FIGS. 5 and 6).

Table II shows the effect of grain refining on the physical characteristics of the alloy. Alloy A in this table has the composition of alloy 1 in Table I; alloy B has the same composition but with 0.2% more palladium and no ruthenium. As shown in the table, grain refining produces an alloy having increased strength, increased elongation and thus increased toughness. An Instron machine was used to measure the values reported. The same improved physical properties were observed when rhenium was used as the grain refining agent, but not when iridium was used.

TABLE II

| Alloy | Yield Strength | Ultimate Tensile Strength | Elongation |
|---|---|---|---|
| A | 150,000 psi | 175,000 psi | 12% |
| B | 130,000 psi | 151,000 psi | 9% |

As mentioned above, the standard technique for forming a grain-refined alloy cannot be employed with the alloys of this invention because it leads to the formation of bubbles in the porcelain during the porcelain firing process. Rather, the grain-refined alloy must be formed either under vacuum or in an inert atmosphere such as an atmosphere of argon. Without proceeding in this way, the alloy absorbs gases from the atmosphere which are later released from the alloy during firing to form bubbles in the porcelain. Note, however, that the improved grain and physical properties described above result whether the alloy is made in air, under vacuum or in an inert atmosphere; it is only so that porcelain can later be applied to a casting made from the alloy that vacuum or an inert atmosphere has to be used in preparing the alloy. Also, the poor grain structure and physical properties described above for iridium result irrespective of whether the alloy is made in air, in vacuum or under an inert atmosphere.

Figure 8:
FIG. 8 is a photograph of the porcelain surface produced when the grain-refined alloy is made in an inert atmosphere.
Figure 9:
FIG. 9 is a photograph of the porcelain surface produced when the grain-refined alloy is made in air.

FIGS. 8 and 9 illustrate the difference between forming the alloy in air and under the conditions of this invention. In each case, the alloy has the composition of alloy 1 in Table I.

FIG. 8 shows the surface of the porcelain when the elements making up the alloy including the grain refining agent are combined under a blanket of an inert gas, such as argon. The argon is preferrably introduced after vacuum has been applied to the melting chamber to remove ambient air. Alternatively, a stream of argon can be passed through the chamber without first drawing a vacuum. As can be seen in FIG. 8, the porcelain is smooth and bubble free. The same smooth porcelain surface also is achieved when the constituents are combined in a vacuum without introducing an inert gas. In this case, the temperature of the melt and the applied vacuum must be controlled in view of the vapor pressures of the components of the alloy to avoid excessive relative losses of the more volatile components.

In comparison to the smooth surface achieved when the alloy is made in an inert temperature or under vacuum, FIG. 9 illustrates what happens to the porcelain if the grain-refined alloy is made in air. Plainly, porcelain with bubbles such as those shown in FIG. 9 would not be acceptable.

In addition to the requirement that the grain refined alloy be made under vacuum or in an inert atmosphere, the grain refining agent must be introduced within a specific range of concentrations. In particular, at least 0.1% of grain refining agent must be added to achieve the improved physical properties and additions above about 0.5% tend to embrittle the alloy.

Although specific embodiments of the invention have been described and illustrated, it is to be understood that modifications can be made without departing from the invention's spirit and scope. Thus the concentrations of palladium, gold, gallium, copper, aluminum, cobalt and ruthenium or rhenium can be varied from the percentages illustrated and alloys having the superior characteristics of the invention will still result. For example, the palladium concentration can be varied at least between 35 and 85% by weight; the copper concentration between 0 and 12%; the gallium concentration between 5 and 15%, the gold concentration between 0 and 50%; the aluminum concentration between 0 and 5%; the cobalt concentration between 0–13%, and the ruthenium or rhenium concentration between 0.1% and 0.5%.

I claim:

1. A grain-refined palladium based dental alloy for porcelain-fused-to-metal restorations consisting by weight of essentially about 35–85% palladium, 0–12% copper, 5–15% gallium, 0–50% gold, 0–5% aluminum, 0–13% cobalt and 0.1–0.5% ruthenium or rhenium, the total of the constituents being 100%.

2. The alloy of claim 1 wherein the ruthenium or rhenium concentration is about 0.2%.

3. The alloy of claim 1 wherein the cobalt concentration is about 2.5%.

4. The alloy of claim 1 wherein the cobalt concentration is about 10%.

5. The alloy of claim 1 wherein the aluminum concentration is about 0.1%.

6. A grain-refined palladium based dental alloy for porcelain-fused-to-metal restorations consisting by weight of essentially about 78.7% palladium, 10% copper, 9.0% gallium, 2.0% gold, 0.1% aluminum, and 0.2% ruthenium or rhenium.

7. A grain-refined palladium based dental alloy for porcelain-fused-to-metal restorations consisting by weight of essentially about 78.7% palladium, 7.5% copper, 9.0% gallium, 2.0% gold, 0.1% aluminum, 2.5% cobalt and 0.2% ruthenium or rhenium.

8. A grain-refined palladium based dental alloy for porcelain-fused-to-metal restorations consisting by weight of essentially about 80.7% palladium, 9.0% gallium, 0.1% aluminum, 10% cobalt and 0.2% ruthenium or rhenium.

9. The alloy of claims 1, 6, 7 or 8 wherein the components of the alloy are combined under vacuum.

10. The alloy of claims 1, 6, 7 or 8 wherein the components of the alloy are combined under an inert atmosphere.

11. The alloy of claim 10 wherein the inert atmosphere includes argon.

12. A grain-refined palladium based dental alloy for porcelain-fused-to-metal restorations consisting by weight of essentially about 35–85% palladium, 0–12% copper, 5–15% gallium, 0–50% gold, an effective amount of aluminum up to about 5% for the purpose of protecting the alloy during melting and the porcelain firing process, 0–13% cobalt and 0.1–0.5% ruthenium or rhenium, the total of the constituents being 100%, wherein the components of the alloy are combined under vacuum or in an inert atmosphere.

* * * * *